(12) United States Patent  
Millerd

(10) Patent No.: US 7,144,387 B2  
(45) Date of Patent: Dec. 5, 2006

(54) BUTTERFLY NEEDLE WITH PASSIVE GUARD

(75) Inventor: Don Millerd, San Diego, CA (US)

(73) Assignee: Visual Connections, San Diego, CA (US)

( * ) Notice: Subject to any disclaimer, the term of this patent is extended or adjusted under 35 U.S.C. 154(b) by 81 days.

(21) Appl. No.: 10/978,614

(22) Filed: Nov. 1, 2004

(65) Prior Publication Data

US 2005/0096606 A1 May 5, 2005

Related U.S. Application Data

(62) Division of application No. 10/434,717, filed on May 9, 2003, now Pat. No. 6,840,920.

(51) Int. Cl.
A61M 5/32 (2006.01)
A61M 5/00 (2006.01)

(52) U.S. Cl. .................. 604/177; 604/165.03; 604/110; 604/198

(58) Field of Classification Search ...................... None
See application file for complete search history.

(56) References Cited

U.S. PATENT DOCUMENTS

| | | | |
|---|---|---|---|
| 3,572,334 A | 3/1971 | Petterson | |
| 4,192,304 A | 3/1980 | Millet | |
| 4,194,504 A | 3/1980 | Harms et al. | |
| 4,362,156 A | 12/1982 | Feller, Jr. et al. | |
| 4,781,692 A | 11/1988 | Jagger et al. | |
| 5,167,635 A | 12/1992 | Haber et al. | |
| 5,176,655 A | 1/1993 | McCormick et al. | |
| 5,222,945 A | 6/1993 | Basnight | |
| 5,232,457 A | 8/1993 | Grim | |
| 5,242,401 A | 9/1993 | Colsky | |
| 5,267,977 A | 12/1993 | Feeney, Jr. | |
| 5,376,080 A | 12/1994 | Petrussa | |
| 5,382,240 A | 1/1995 | Lam | |
| 5,389,085 A | 2/1995 | D'Alessio et al. | |
| 5,403,286 A | 4/1995 | Lockwood, Jr. | |
| 5,498,241 A * | 3/1996 | Fabozzi | 604/177 |
| 5,549,571 A | 8/1996 | Sak | |
| 5,582,597 A | 12/1996 | Brimhall et al. | |
| 5,591,138 A | 1/1997 | Vaillancourt | |
| 6,139,532 A | 10/2000 | Howell et al. | |
| 6,210,371 B1 * | 4/2001 | Shaw | 604/164.08 |
| D452,000 S | 12/2001 | Crawford et al. | |
| D452,001 S | 12/2001 | Crawford et al. | |
| 6,375,640 B1 | 4/2002 | Teraoka | |
| 6,379,336 B1 | 4/2002 | Asbaghi et al. | |
| 2003/0225375 A1 * | 12/2003 | Coleman et al. | 604/165.03 |

* cited by examiner

*Primary Examiner*—Michael J. Hayes
(74) *Attorney, Agent, or Firm*—Nydegger & Associates

(57) ABSTRACT

A butterfly needle device having a passive needle protection system includes a needle that has a proximal end, a distal tip and defines a needle axis. A cylindrical base member having an axially aligned groove is disposed over the needle with a first wing extending radially from the base member. A second wing is provided for rotation about the needle axis relative to the first wing between a closed configuration in which the wings are juxtaposed and an open configuration in which the wings are displaced from each other. A cylindrical needle guard having a plug is disposed over the needle. A spring biases the needle guard distally relative to the base member. A wing-activated mechanism is provided to align the plug with the groove after a closed-open-closed wing cycle allowing the needle guard to distally advance to cover the needle tip at the end of the cycle.

9 Claims, 2 Drawing Sheets

BUTTERFLY NEEDLE WITH PASSIVE GUARD

This application is a divisional of application Ser. No. 10/434,717, filed May 9, 2003, now U.S. Pat. No. 6,840,920. The contents of application Ser. No. 10/434,717 are incorporated herein by reference.

FIELD OF THE INVENTION

The present invention pertains generally to butterfly needle devices (including winged needles and winged I.V. sets) for medical use. More particularly, the present invention pertains to passive safety systems for butterfly needle devices. The present invention is particularly, but not exclusively, useful for passively covering and protecting the needle of a butterfly needle device after the device has been used in a medical procedure.

BACKGROUND OF THE INVENTION

Accidental needle sticks can occur in several ways. For example, a sudden movement by a patient can cause a healthcare worker to lose control of the needle, resulting in injury. Additionally, injuries can result when contaminated, unprotected needles are left unattended or disposed of improperly. Moreover, attempts to manually recap a needle after a medical procedure can also result in injury. In addition to accidental needle sticks, unnecessary exposure to bloodborne pathogens can result when a healthcare worker mistakenly re-uses a contaminated needle on a patient.

Accidental needle sticks and the inadvertent reuse of a contaminated needle have the potential to expose patients and healthcare workers to life-threatening viruses that include hepatitis and HIV. Because of this potential exposure, healthcare providers are obligated to conduct extensive testing of exposed individuals. Additional follow-up testing for HIV is typically prescribed approximately six months after the exposure. It is to be appreciated that the costs associated with the testing, lab work, the workers lost time, and the associated tracking and administrative costs, can be considerable.

One type of needle device that can cause accidental needle sticks is the butterfly needle. The butterfly needle is typically used when it is required to introduce a fluid into or withdraw a fluid from a patient over a relatively long period of time. For example, the butterfly needle can be connected to a syringe, an IV set or a blood collection holder. One advantageous feature of a butterfly needle is that it contains wings that can be folded flat and taped to the patient's skin to stabilize the device. This is especially important when the needle must remain in place for a relatively long period. Typically, the wings of a butterfly needle are initially juxtaposed to allow the healthcare worker to hold the device during insertion of the needle into the patient. After needle insertion, the wings are folded flat against the patient's skin and taped. To remove the butterfly needle, the tape is pulled up and the wings are folded together (i.e. juxtaposed). With the wings together, the needle can be easily withdrawn from the patient.

In light of the above, it is an object of the present invention to provide a passive needle protection system for a butterfly needle that is activated by the normal opening and closing of the butterfly needle wings. It is yet another object of the present invention to provide a needle protection system for a butterfly needle device that locks a guard in place to cover and protect the tip of the needle and to prevent inadvertent reuse of the device. Yet another object of the present invention is to provide a protective device for a butterfly needle that is easy to use, relatively simple to implement and comparatively cost effective.

SUMMARY OF THE PREFERRED EMBODIMENTS

A butterfly needle device having a passive needle protection system includes an elongated needle that has a proximal end, a distal tip and defines a needle axis. The device further includes a hollow, cylindrical base member that is disposed over the needle and centered on the needle axis. A substantially flat first wing is attached to and extends radially from the cylindrical base member. The device further includes a first hollow cylinder that is disposed over the needle proximal to the base member and is centered on the needle axis. A second substantially flat wing is attached to and extends radially from the first hollow cylinder.

The above-described interactive cooperation of structure allows the second wing to rotate about the needle axis relative to the first wing. More specifically, the second wing can rotate relative to the first wing between a first, closed configuration in which the wings are juxtaposed and a second, open configuration in which the wings are displaced from each other by approximately one-hundred eighty degrees (180°). The closed configuration allows the healthcare worker to easily grip the wings when the needle is inserted into and withdrawn from the patient. On the other hand, the open configuration allows the wings to be taped to the patient to stabilize the device during a medical procedure which can involve the introduction of a medicament into the patient or the aspiration of a body fluid from the patient.

The device also includes a hollow, cylindrical needle guard that is disposed over the needle and positioned coaxially with the base member and first hollow cylinder. For the butterfly needle device, the needle guard is sized to pass through both the base member and first hollow cylinder, thus allowing for reciprocal axial movement of the guard relative to the base member and first hollow cylinder. In one embodiment of the device, the base member has a cylindrical shaped inner wall that is formed with an axially aligned groove that extends from the base member's proximal end to the base member's distal end. A plug extends radially from the needle guard for interaction with the groove formed on the base member.

Also for the butterfly needle device, a helical spring is provided to bias the needle guard distally relative to the base member. In a typical embodiment of the device, the helical spring is interposed between the needle guard and a needle/tubing adapter that is attached to the proximal end of the needle. With this structural combination, the needle guard is biased in the distal direction relative to the needle, the base member, the wings and the first hollow cylinder.

The device further includes a mechanism for rotating the needle guard (about the needle axis) to align the plug with the groove after the wings have been cycled from the closed configuration to the open configuration and then back to the closed configuration. This alignment of the plug and groove at the completion of the closed-open-closed wing cycle allows the needle guard to distally advance relative to the needle. Thus, at the end of the closed-open-closed wing cycle, the needle guard is free to advance to a distal position wherein the needle guard covers and protects the distal tip of the needle.

In greater structural detail, the aligning mechanism includes the first hollow cylinder (see partial description above) and a second hollow cylinder. The first hollow cylinder has an inner wall that is formed with an axially aligned slot that is provided to interact with the plug. With the plug in the slot, the guard rotates relative to the base member during movement of the second wing relative to the first wing. For the butterfly needle device, the second hollow cylinder is attached to the first wing and centered on the needle axis proximal to the first hollow cylinder. The second hollow cylinder has an inner wall that is formed with a channel for interaction with the plug.

In order, starting at the proximal end of the device and proceeding distally, the device includes the second hollow cylinder, the first hollow cylinder, and then the base member. Of these elements, the second hollow cylinder and the base member are attached to and rotate with the first wing while the first hollow cylinder, the needle/tubing adapter and the needle are attached to the second wing. Together, the first and second hollow cylinders and the base member form a continuous passageway that is sized to allow the cylindrical needle guard to axially travel through the passageway.

In use, the plug is initially located in the channel of the second hollow cylinder and the wings are juxtaposed (i.e. positioned in the closed configuration). Next, the distal tip of the needle is inserted into the patient. With the needle inserted, the wings are rotated open, causing the second hollow cylinder to rotate relative to the first hollow cylinder. At the end of this rotation, the channel and slot are aligned. Accordingly, the plug advances distally from the channel and into the slot. After an injection or withdrawal of fluid from the patient, the wings are rotated closed. As the healthcare worker closes the wings, the first hollow cylinder rotates relative to the base member and when the wings are juxtaposed, the slot in the first hollow cylinder aligns with the groove in the base member. With this alignment, the plug (and needle guard) are free to advance distally until the needle guard is positioned over the distal tip of the needle.

The butterfly needle device can further include a locking mechanism to lock the needle guard in place once the needle guard has advanced into position covering the distal tip of the needle. In greater structural detail, the locking mechanism can include a deflectable tab that extends from the needle guard and terminates in a tab end. Specifically, the tab is deflectable from a first position wherein the tab end is distanced from the needle axis by a distance $d_1$, to a second position wherein the tab end is distanced from the needle axis by a distance $d_2$, with $d_1 > d_2$. A catch recess is formed in the base member to receive the tab when the needle guard is in position covering the distal tip of the needle. The catch recess prevents proximal movement of the tab, and thus, once the tab is in the catch recess, the needle guard is locked over the needle to protect against accidental needle sticks or inadvertent re-use.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
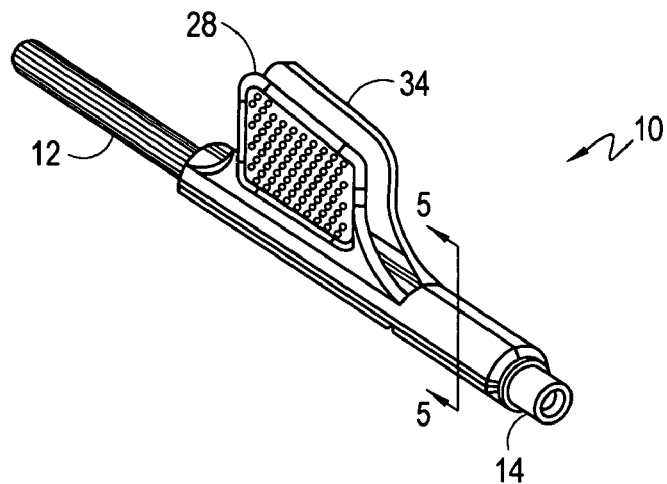
FIG. 1 is a perspective view of a butterfly needle device having a passive needle protection system shown.

Referring initially to FIG. 1, a butterfly needle device having a passive needle protection system is shown and generally designated 10. FIG. 1 shows the device 10 configured for delivery to the healthcare worker. As shown, the device 10 is typically shipped with a protective cap 12 that covers and protects the needle tip during handling. In the embodiment of the device 10 shown, a needle/tubing adapter 14 is included allowing the device 10 to be connected to a universal Luer lock using microtubing, which in turn can be connected to an IV set, blood collection holder, syringe, etc.

Figure 2:
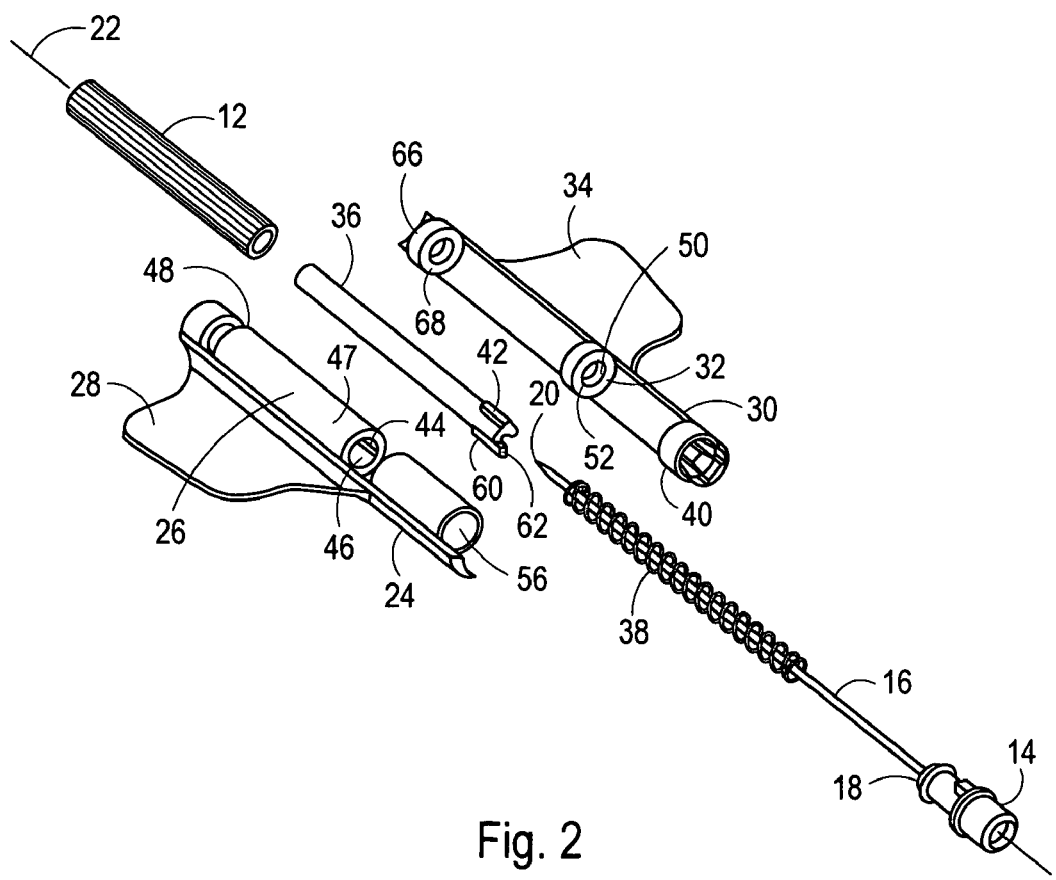
FIG. 2 is an exploded perspective view of a butterfly needle device having a passive needle protection system.

As best seen in FIG. 2, the device 10 includes an elongated needle 16 that has a proximal end 18, a distal tip 20 and defines a needle axis 22. The device 10 further includes a first winged element 24, which in this case is formed with a hollow, cylindrical base member 26. As further shown, the first winged element 24 also includes a substantially flat first wing 28 that is attached to, and extends radially from, the cylindrical base member 26. During assembly of the device 10, the base member 26 is disposed over the needle 16 and centered on the needle axis 22.

Continuing with reference to FIG. 2, it can be seen that the device 10 also includes a second winged element 30, which for the embodiment shown is formed with a first hollow cylinder 32. As further shown, the second winged element 30 further includes a substantially flat second wing 34 that is attached to, and extends radially from, the first hollow cylinder 32. During assembly of the device 10, the first hollow cylinder 32 is disposed over the needle 16 (proximal to the base member 26) and is centered on the needle axis 22.

FIG. 2 further shows that the device 10 includes a hollow, cylindrical needle guard 36 that is disposed over the needle 16 and positioned coaxially with the base member 26 and the first hollow cylinder 32 (when assembled). As shown, the needle guard 36 is sized to pass through both the base member 26 and the first hollow cylinder 32, thus allowing for reciprocal axial movement of the needle guard 36 relative to both the base member 26 and first hollow cylinder 32.

Also shown in FIG. 2, the butterfly needle device 10 can include a helical spring 38 to bias the needle guard 36 distally relative to the base member 26 and first hollow cylinder 32. When the device 10 is assembled, the proximal end 18 of the needle 16 is attached to the needle/tubing adapter 14, which in turn, includes a tapered distal portion for mounting the adapter 14 to the second winged element 30 via socket 40. A stop (not shown) can be formed on the adapter 14 to limit the rotation of the wings 28, 34 during opening to thereby prevent the winged elements 24, 30 from pinching the patient's skin. Thus, the second winged element 30 which includes the first hollow cylinder 32 and the socket 40 rotate together relative to the first winged element 24. After device 10 assembly, the helical spring 38 is interposed between the needle guard 36 and the needle/tubing adapter 14. With this structural combination, the needle guard 36 is biased in the distal direction relative to the needle 16, the needle/tubing adapter 14, the first winged element 24 and the second winged element 30.

Figure 3:
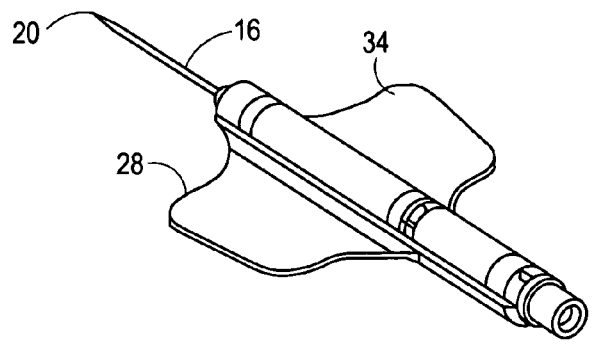
FIG. 3 is a perspective view of a butterfly needle device having a passive needle protection system shown with the wings in the open configuration.
Figure 4:
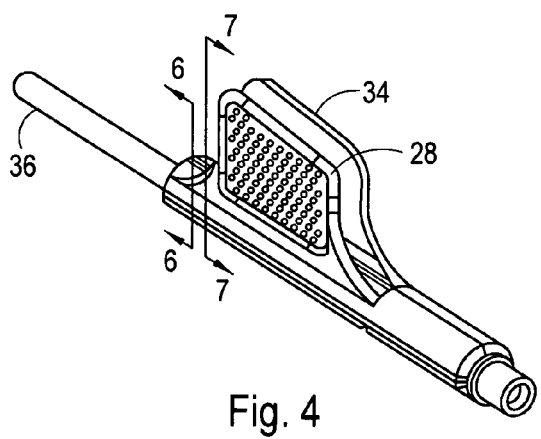
FIG. 4 is a perspective view of a butterfly needle device having a passive needle protection system shown with the wings in the closed configuration and the needle guard positioned to cover the distal tip of the needle.

As indicated above with reference to FIG. 1, the device 10 is initially prepared in a closed configuration wherein the first wing 28 and second wing 34 are juxtaposed. This closed configuration allows the healthcare worker to easily grip the wings 28, 34 during insertion of the needle 16 (needle 16 shown FIG. 2) into the patient. With the needle 16 inserted, the second wing 34 is rotated relative to the first wing 28 to an open configuration (shown in FIG. 3) in which the wings 28, 34 are displaced from each other by approximately one-hundred eighty degrees (180°). This open configuration allows the wings 28, 34 to be taped to the patient (tape and patient not shown) to stabilize the device 10 while fluids are introduced into or withdrawn from the patient. Next, the tape is removed and the second wing 34 is rotated relative to the first wing 28 to reconfigure the device 10 back into the closed configuration (shown in FIG. 4) in which the wings 28, 34 are once again juxtaposed. FIG. 4 shows that at the end of the closed-open-closed cycle, the needle guard 36 has advanced into a distal position wherein the needle guard 36 covers and protects the distal tip 20 of the needle 16.

The device 10 further includes a mechanism for regulating the distal movement of the needle guard 36 during the closed-open-closed cycle. Specifically, as best seen in FIG. 2, the needle guard 36 is formed with a plug 42 that extends radially outward from the cylindrical portion of the needle guard 36. The plug 42 is sized to move within an axially aligned groove 44 that is formed on the inner wall 46 of the base member 26. For the embodiment shown, the axially aligned groove 44 extends from the proximal end 47 of the base member 26 to the distal end 48 of the base member 26. Also shown in FIG. 2, the first hollow cylinder 32 has an inner wall 50 that is formed with an axially aligned slot 52 for interaction with the plug 42. In addition, the first winged element 24 includes a second hollow cylinder 54 that is centered on the needle axis 22 proximal to the first hollow cylinder 32, after assembly of the device 10. As best seen with cross-reference to FIGS. 2 and 5, the second hollow cylinder 54 has an inner wall 56 that is formed with a channel 58 for interaction with the plug 42.

Figure 5:
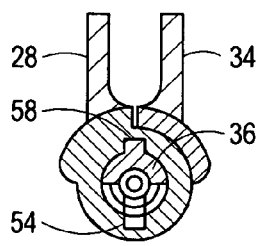
FIG. 5 is a cross sectional view of a butterfly needle device as seen along line 5—5 in FIG. 1.

With cross-reference to FIGS. 1 and 5, it can be seen that the plug 42 is initially located in the channel 58 of the second hollow cylinder 54 and the wings 28, 34 are juxtaposed (i.e. positioned in the closed configuration). In this configuration, the cap 12 can be removed and the distal tip 20 of the needle 16 can be inserted into the patient. With the needle 16 inserted, the wings 28, 34 are rotated open to the configuration shown in FIG. 3. This rotation causes the second hollow cylinder 54 to rotate relative to the first hollow cylinder 32 (shown in FIG. 2). At the end of this rotation, the channel 58 and slot 52 (shown in FIG. 2) are aligned. Accordingly, the plug 42 advances distally from the channel 58 and into the slot 52. After an injection or withdrawal of fluid from the patient, the wings 28, 34 are rotated closed. As the wings 28, 34 are closed, the first hollow cylinder 32 rotates relative to the base member 26 and when the wings 28, 34 are juxtaposed as shown in FIGS. 1 and 4, the slot 52 (see FIG. 2) in the first hollow cylinder 32 aligns with the groove 44 in the base member 26. With this alignment, the plug 42 (and needle guard 36) is free to advance distally until the needle guard 36 is positioned over the distal tip 20 of the needle 16, as shown in FIG. 4.

Figure 6:
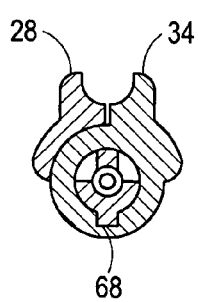
FIG. 6 is a cross sectional view of a butterfly needle device as seen along line 6—6 in FIG. 4.
Figure 7:
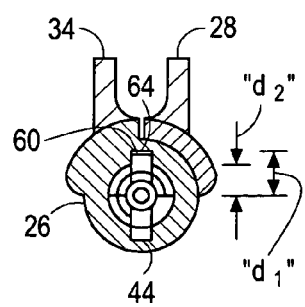
FIG. 7 is a cross sectional view of a butterfly needle device as seen along line 7—7 in FIG. 4.

With cross-reference now to FIGS. 2, 6 and 7, it can be seen that the butterfly needle device 10 can further include a locking mechanism to lock the needle guard 36 once the needle guard 36 has advanced into position covering the distal tip 20 of the needle 16. The locking mechanism can also lock the wings 28, 34 in the closed configuration. For the embodiment shown, the locking mechanism includes a deflectable tab 60 that extends from the cylindrical portion of the needle guard 36 and terminates in a tab end 62. Specifically, the tab 60 is deflectable from a first position wherein the tab end 62 is distanced from the needle axis 22 by a distance $d_1$, to a second position wherein the tab end 62 is distanced from the needle axis 22 by a distance $d_2$, with $d_1 > d_2$. FIG. 7 shows that a catch recess 64 is formed in the base member 26 to receive the tab 60 when the needle guard 36 is in position covering the distal tip 20 of the needle 16. The catch recess 64 prevents proximal movement of the tab 60, and thus, once the tab 60 is in the catch recess 64, the needle guard 36 is locked over the needle 16 to protect against accidental needle sticks or inadvertent re-use.

To lock the wings 28, 34, the second winged element 30 can include a locking cylinder 66 that is positioned distally relative to the base member 26 and centered on the axis 22 when the device 10 is assembled. The locking cylinder 66 is formed with a keyway 68 that is aligned with the groove 44 when the wings 28, 34 are juxtaposed. When the needle guard 36 is in a distal position covering the tip 20 of the needle 16, a portion of the plug 42 is in the keyway 68 and a portion of the plug 42 is in the groove 44 preventing rotational movement of wing 28 relative to wing 34.

While the particular devices and methods as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A butterfly needle device having a passive needle protection system comprising:

an elongated needle having a proximal end and a distal tip, said needle defining an axis;

a hollow, cylindrical base member disposed over said needle and centered on said axis;

a first wing extending from said cylindrical base member;

a second wing positioned in said cylindrical base member for rotation about said axis relative to said first wing between a closed configuration wherein said wings are juxtaposed and an open configuration wherein said wings are displaced from each other by approximately one-hundred eighty degrees (180°);

a hollow cylindrical needle guard disposed on said needle and positioned coaxially with said base member for reciprocal axial movement relative thereto, with one of said base member and said needle guard formed with a plug and the other formed with an axially aligned groove for interaction with said plug;

a means for biasing said needle guard distally relative to said base member;

a means for aligning said plug with said groove after said wings have been cycled from said closed configuration to said open configuration and then back to said closed configuration to allow distal advancement of said needle guard relative to the needle after said cycle to cover and protect said distal tip of said needle with said needle guard; and a means for locking said needle guard in position covering said distal tip of said needle.

2. A butterfly needle device as recited in claim 1 further comprising a needle/tubing adapter attached to said proximal end of said needle, and wherein said biasing means comprises a spring disposed between said needle/tubing adapter and said needle guard.

3. A butterfly needle device as recited in claim 1 wherein said plug extends radially from said needle guard and said base member has an inner wall formed with said axially aligned groove.

4. A butterfly needle device as recited in claim 3 wherein said aligning means comprises a hollow cylinder attached to said second wing and positioned coaxially with said guard, said hollow cylinder formed with a slot for interaction with said plug to rotate said guard relative to said base member to align said plug with said groove after a movement of said second wing relative to said first wing.

5. A butterfly needle device as recited in claim 4 wherein said hollow cylinder is a first hollow cylinder and said aligning means further comprises a second hollow cylinder attached to said first wing and positioned coaxially with said guard, said second hollow cylinder formed with a channel for interaction with said plug to rotate said guard relative to said first hollow cylinder to align said plug with said slot after a movement of said second wing relative to said first wing.

6. A butterfly needle device as recited in claim 1 wherein said locking means comprises a tab extending from said needle guard to a tab end, said tab deflectable from a first position wherein said tab end is distanced from said axis by a distance $d_1$, to a second position wherein said tab end is distanced from said axis by a distance $d_2$, with $d_1 > d_2$, said locking means further comprising a catch recess formed in said base member to receive said tab and lock said needle guard.

7. A butterfly needle device having a passive needle protection system comprising:

an elongated needle having a proximal end and a distal tip, said needle defining an axis;

a hollow base member disposed over said needle and formed with an axially aligned groove;

a first wing extending from said base member;

a second wing positioned on said base member;

a hollow cylindrical needle guard disposed on said needle and positioned coaxially with said base member for reciprocal axial movement relative thereto, said needle guard formed with a plug for movement in said axially aligned groove;

a spring for biasing said needle guard distally relative to said base member;

a hollow cylinder attached to said second wing and positioned proximal to said base member, said hollow cylinder formed with a slot for holding said plug to rotate said guard about said axis relative to said base member and align said plug with said groove after a pre-selected movement of said second wing relative to said first wing; and a means for locking said first wing in a fixed position relative to said second wing after said pre-selected movement of said second wing relative to said first wing.

8. A butterfly needle device as recited in claim 7 further comprising a means for locking said needle guard in position covering said distal tip of said needle.

9. A butterfly needle device as recited in claim 8 wherein said needle guard locking means comprises a tab extending from said needle guard to a tab end, said tab deflectable from a first position wherein said tab end is distanced from said axis by a distance $d_1$, to a second position wherein said tab end is distanced from said axis by a distance $d_2$, with $d_1 > d_2$, said locking means further comprising a catch recess formed in said base member to receive said tab and lock said needle guard.

* * * * *